United States Patent
Chu et al.

(10) Patent No.: US 7,902,145 B2
(45) Date of Patent: Mar. 8, 2011

(54) TERMINAL STERILIZATION OF INJECTABLE COLLAGEN PRODUCTS

(75) Inventors: George Chu, Carlsbad, CA (US); C. Randall Harrell, Tarpon Springs, FL (US); Hector J. Gomez, Lutz, FL (US)

(73) Assignee: Albiorex, LLC, Clear Water, FL (US)

( * ) Notice: Subject to any disclaimer, the term of this patent is extended or adjusted under 35 U.S.C. 154(b) by 985 days.

(21) Appl. No.: 11/383,845

(22) Filed: May 17, 2006

(65) Prior Publication Data

US 2006/0280769 A1     Dec. 14, 2006

Related U.S. Application Data

(60) Provisional application No. 60/682,507, filed on May 19, 2005.

(51) Int. Cl.
*C12M 1/12*     (2006.01)
*A61K 38/00*     (2006.01)

(52) U.S. Cl. ............... 514/2; 435/1.3; 435/31; 435/446; 435/287.4; 530/356

(58) Field of Classification Search ............... None
See application file for complete search history.

(56) References Cited

U.S. PATENT DOCUMENTS

| | | | | |
|---|---|---|---|---|
| 4,320,201 A | * | 3/1982 | Berg et al. ............... | 435/265 |
| 4,620,908 A | | 11/1986 | Van Duzer et al. | |
| 5,460,962 A | * | 10/1995 | Kemp ............... | 435/238 |
| 6,231,613 B1 | | 5/2001 | Greff et al. | |
| 6,908,591 B2 | | 6/2005 | MacPhee et al. | |
| 7,064,187 B2 | * | 6/2006 | Stone ............... | 530/355 |
| 2003/0003157 A1 | * | 1/2003 | Ohan et al. ............... | 424/499 |
| 2004/0033160 A1 | | 2/2004 | MacPhee et al. | |
| 2004/0192603 A1 | * | 9/2004 | Stone ............... | 514/12 |

FOREIGN PATENT DOCUMENTS

WO    WO 98/31403    7/1998

OTHER PUBLICATIONS

Roberts et al. (1998) Virginia Cooperative Extension, Publication No. 458-300, Virginia Tech., pp. 1-3.*
Forum Archives (2008, updated) "Importance of a freeze-thaw cycle", http://www.protocol-online.org/biology-forums/posts/10588.html, p. 1.*
Hamer, et al. "Changes in allograft bone irradiated at different temperatures", *J. Bone Joint Surg. Br.*, 81(2):342-4 (1999).

* cited by examiner

*Primary Examiner* — Anand U Desai
*Assistant Examiner* — Samuel Liu
(74) *Attorney, Agent, or Firm* — Benjamin Aaron Adler

(57) ABSTRACT

Methods of sterilizing dermal fillers and injectable collagen material have been developed which reduce the level of active biological contaminants or pathogens without adversely affecting the material, i.e., wherein the dermal fillers and injectable collagen material retain their same properties before and after its terminal sterilization. In one embodiment the method for sterilizing the dermal filler or injectable collagen material that is sensitive to radiation contains the steps of protecting the filler or material from radiation, and irradiating the filler or material with a suitable dose of radiation for a time and at a rate effective to sterilize the filler or injectable material. In a preferred embodiment the method for sterilizing the dermal filler or injectable collagen material that is sensitive to radiation includes the steps of a) freezing the filler or material at a temperature below its freezing temperature, which is generally below 0° C. and b) irradiating the filler or material with a suitable dose of radiation at an effective rate for a time effective to sterilize the filler or material. The exposure of the radiation differs depending upon the density of the filler or material, but is preferably between 5 kGy and 12 kGy and more preferably between 6 kGy and 8 kGy. These doses result in a sterility assurance level (SAL) of $10^{-6}$ SAL for the filler or material.

14 Claims, No Drawings

TERMINAL STERILIZATION OF INJECTABLE COLLAGEN PRODUCTS

CROSS-REFERENCE TO RELATED APPLICATIONS

This application claims priority to U.S. Ser. No. 60/682,507 filed May 19, 2005.

FIELD OF THE INVENTION

The present invention relates to methods for sterilizing injectable collagen materials and dermal fillers.

BACKGROUND OF THE INVENTION

It is often difficult to sterilize biologically active compounds since the chemical, physical or physiological properties of active compounds are often significantly altered by variations in the compounds surrounding environment. For example, changes in pH, ionic strength, or temperature can result in reversible or irreversible changes in the character of compounds.

Radiation sterilization has the advantages of high penetrating ability, relatively low chemical reactivity, and instantaneous effects without the need to control temperature, pressure, vacuum, or humidity. Radiation sterilization is widely used in industry for a variety of products and both dosage levels and its biological effects are well known. It is generally agreed that electron-beam and gamma sterilization are equally effective in killing microbial organisms. While sufficient to effectively kill microorganisms, the radiation generally alters the structure of proteins, DNA, RNA, etc. as to render it biologically inactive. Therefore there remains a significant need for a simple way to effectively and safely sterilize biologically active compounds without deleteriously affecting their chemical, physical, or physiological properties.

Most injectable collagen materials for human use are prepared by an aseptic process and cannot be submitted to terminal sterilization. Accordingly, they may contain unwanted and potentially dangerous biological contaminants or pathogens, such as viruses, bacteria (including inter- and intracellular bacteria, such as mycoplasmas, ureaplasmas, nanobacteria, chlamydia, rickettsias), yeasts, molds, fungi, single or multicellular parasites, and/or similar agents which, alone or in combination may cause adverse reactions. Consequently, it is of utmost importance that any biological contaminant in the injectable collagen material be inactivated before the product is used. This is especially critical when the material is to be administered directly to a patient.

Most procedures for producing injectable collagen materials have involved methods that screen or test the starting materials for one or more particular biological contaminants or pathogens. Materials that test positive for a biological contaminant or pathogen are discarded. Examples of screening procedures include the testing for a particular virus in the starting material such as human placenta. Then the manufacturing process must include steps for removal or inactivation of the contaminant(s) and/or pathogen(s) from the initial raw material.

Most injectable collagen products on the market are made from a material which is initially sterilized by means such as by filtration of an initial collagen solution, then is processed totally under sterile conditions. A sterility assurance level (SAL) of $10^{-6}$ SAL is very difficult to achieve using this process. Results with gamma ray or e-beam irradiation are much better, but the collagen material is frequently damaged using these methods.

In view of the difficulties discussed above, there remains a need for methods of terminal sterilizing injectable collagen material without an adverse effect on the material's desirable attributes.

It is therefore an object of the present invention to provide methods of sterilizing injectable collagen material by reducing the level of active biological contaminants or pathogens without adversely affecting the material.

BRIEF SUMMARY OF THE INVENTION

Methods of sterilizing dermal fillers and injectable collagen material have been developed which reduce the level of active biological contaminants or pathogens without adversely affecting the material, i.e., wherein the dermal fillers and injectable collagen material retain their same properties before and after its terminal sterilization. In one embodiment the method for sterilizing the dermal filler or injectable collagen material that is sensitive to radiation contains the steps of protecting the filler or material from radiation, and irradiating the filler or material with a suitable dose of radiation for a time and at a rate effective to sterilize the filler or injectable material. In a preferred embodiment, the method for sterilizing the dermal filler or injectable collagen material that is sensitive to radiation includes the steps of a) freezing the filler or material at a temperature below its freezing temperature, which is generally below 0° C., and b) irradiating the filler or material with a suitable dose of radiation at an effective rate for a time effective to sterilize the filler or material. The exposure of the radiation differs depending upon the density of the filler or material, but is preferably between 5 kGy and 12 kGy and more preferably between 6 kGy and 8 kGy. These doses result in a sterility assurance level (SAL) of $10^{-6}$ SAL for the filler or material.

DETAILED DESCRIPTION OF THE INVENTION

Dermal Fillers and Injectable Collagen

As generally used herein, "injectable collagen" includes, but is not limited to, collagen pastes, gels, solutions, or suspensions, homogeneous or heterogeneous, which are contained in syringes, tubes or other containers equipped with appropriate plungers or systems, designed to extrude the collagen through a fine needle or a nozzle. The injectable collagen is designed for injection, surgical application through a trocar, or direct application on a wound surface.

Representative collagen materials include recombinant human collagen, tissue engineered human-based collagen, porcine collagen, human placental collagen, bovine collagen, autologous collagen, collagen fibers, and human tissue collagen matrix. Suitable types of dermal fillers and injectable collagen materials include, but are not limited to, recombinant human collagen type I, recombinant human collagen type III, tissue engineered human-based collagen type I, porcine collagen type I, porcine collagen type III, human type IV placental collagen, for example, at a 2% concentration at neutral pH in phosphate buffered saline ("PBS"), solubilized elastin peptides with bovine collagen, and bovine collagen including ZYDERM® I, ZYDERM® II, and ZYPLAST® collagen implants. ZYDERM® I contains 95-98% type I collagen, with type III collagen as the remainder. It also contains 0.3% lidocaine. ZYDERM® I is 3.5% bovine dermal collagen by weight suspended in physiologic phosphate-buffered sodium chloride solution. ZYDERM® II is identical to ZYDERM® I except that it is 6.5% bovine dermal collagen by weight. ZYPLAST® is 3.5% bovine dermal collagen cross-linked by glutaraldehyde to form a latticework and a more viscous compound.

Other dermal fillers and injectable collagen materials include polymethylmethacrylate microspheres suspended in bovine collagen, collagen fibers prepared from the patient's tissue, human tissue collagen matrix derived from cadaveric dermis suspended in a neutral pH buffer that contains matrix proteins, such as elastin and ground substance components, acellular human cadaveric dermis that has been freeze-dried and micronized, globin (the protein portion of hemoglobin), and cultured autologous fibroblasts. Non-animal derived materials include dextran beads suspended in hylan gel of nonanimal origin, polylactic acid, silicones made of man-made polymers in the form of solids, gels, or liquids as a function of polymerization and cross-linkage, expanded polytetrafluoroethylene (e-PTFE) for facial plastic and reconstructive surgery, in the form of sheets, strips, and tubes. Dermal fillers also include compositions for soft tissue augmentation disclosed in U.S. Pat. No. 6,231,613 to Greff, et al., which are polymers having a water equilibrium content of less than about 15%. Exemplary polymers include cellulose acetates, ethylene vinyl alcohol copolymers polyalkyl ($C_1$-$C_6$) acrylates, acrylate copolymers, and polyalkyl alkacrylates wherein the alkyl and the alkyl groups contain no more than 6 carbon atoms.

Methods for Sterilization of Collagen Material

Methods of sterilizing dermal fillers and injectable collagen material by reducing the level of active biological contaminants or pathogens without adversely affecting the material have been developed. The dermal fillers and injectable collagen material may be decontaminated or sterilized without significantly affecting the physiological properties of the collagen using gamma or electron-beam radiation. The mixture is irradiated under conditions that inactivate any pathogenic microorganisms, viruses, and polynucleotide fragments thereof, DNA or RNA, whether single or double stranded present within the mixture.

Gamma ray or electron beam radiation differs depending upon the density of the filler or material, but is preferably at least 5 kGy. Irradiation of more that 12 kGy is not preferred because the filler or material may be damaged. The most preferred exposure is between about 6 kGy and 8 kGy.

The dermal fillers or injectable collagen material that is sensitive to radiation is treated to protect it from the radiation, then irradiated for a time and at a rate effective to sterilize the filler or injectable material. In the preferred embodiment, the dermal filler or injectable collagen material that is sensitive to radiation is first frozen at a temperature below its freezing temperature, which is generally below 0° C., and irradiated with a suitable radiation at an effective rate for a time effective to sterilize the filler or material material. In an alternative embodiment, cryoprotectants and/or stabilizers like mannitol, mannose, ascorbic acid, hyaluronic acid, or other saccharides or polysaccharides are added to the initial collagen material before its freezing. These protecting agents are neither sufficient in the absence of freezing, nor necessary to get significant protection from irradiation, but may be advantageous.

The irradiated dermal filler or collagen material can be analyzed by SDS polyacrylamide gel electrophoresis and/or differential scanning calorimetry to select the optimal irradiation conditions and demonstrate the preserved quality of the collagen molecules. As used herein, without significant damage means that less than 25%, more preferably 15% or less, of the collagen material or dermal filler is deteriorated or degraded.

Suitable injectable collagen products include, but are not limited to, collagen pastes, gels, solutions, or suspensions, homogeneous or heterogeneous, which are contained in syringes, tubes or other containers equipped with appropriate plungers or systems, designed to extrude their collagen content through a fine needle or a nozzle. The injectable collagen is designed for injection, surgical application through a trocar, or direct application on a wound surface. According to the methods described herein, the collagen paste, gel, solution or suspension will keep the same fluidity before and after its terminal sterilization.

The dermal filler and collagen material, once sterilized, is maintained in a sterile surrounding until used by a caregiver. Illustrative containers include vials, plates, pouches, jars, syringes, etc. Preferably, the container is transparent to both gamma-rays and electron-beams.

The methods described above will be further understood with reference to the following non-limiting examples.

EXAMPLES

Example 1

Injectable Collagen Product, HUMALLAGEN™, Exposed to Irradiation at 25 Kgy

Materials and Methods

A 0.3% to 0.5% human type I+III collagen solution was prepared at pH 3 (lower than 5), filtered through a 0.45 µm porous membrane, and then processed under a laminar flow hood in a class 1000 clean room. No bacteria were detectable in the filtered solution. The collagen was precipitated by addition of 20 mM sodium phosphate, at pH 7.2, at room temperature. The collagen paste was harvested by centrifugation in closed and sterile buckets. The 6% concentrated collagen paste was then washed and diluted to 3.5% with a sterile phosphate buffered physiological solution (PBS). Sterile 1 ml syringes were filled with the final collagen paste. After one week of storage at +4° C., each syringe was packed within its final pouch and sealed before being frozen in dry ice to about −80° C. Each layer of syringes was covered by a one inch thick layer of dry ice, within an insulated polystyrene box. The total height of the final package was less than 15 inches and it was stored at −20° C. or in dry ice until gamma-irradiation. Gamma-irradiation was performed at room temperature for less than 24 hours. The irradiation dose was >25 kGray. Some dry ice was still present in the package after irradiation and the syringes were still frozen. After thawing, the syringes were inspected. The syringes were not damaged and they were stored at room temperature for one week before being tested. The collagen paste was tested using Sodium Dodecyl Sulfate-PolyAcrylamide Gel Electrophoresis (SDS-PAGE) procedures well known to one or ordinary skill in the art.

Results and Discussion

Following irradiation of the syringes containing the collagen paste, the color of the glass syringe turned to light brown. The content of the syringe appeared homogeneous, without significant phase separation between a water phase and the collagen mass. The content could be extruded through a fine gauge needle.

As determined by SDS-PAGE analysis, the collagen molecules are protected significantly by the frozen conditions during the gamma ray irradiation at 25 kGy. Only small amount of the material is degraded, approximately 15% of the total material.

DSC (Differential Scanning Calorimetry) was used to evaluate the collagen material. The reconstituted fibrillar collagen preparation contains a heterogeneous fibril population, possibly including molecules in a nonfibrillar state. The fibrillar classes may represent three or more types of banded and non-banded species that differ from each other in packing order, collagen concentration, fibril width, and level of cross-linking. The multiple melting endotherms of fibrillar collagen product are due to sequential melting of molecular and fibril classes, each with a distinct melting temperature. Peaks at below 36° C. indicate denatured collagen present. A small shoulder at 36° C.-40° C. most likely represents shortened or nicked collagen helices, degraded but not denatured collagen molecules. Nonfibrillar collagen or thin collagen fiber materials are melted at 40 to 45° C. Large fibrillar collagen classes are melted at greater than 45° C.

Table 1. DSC Data for Irradiated Collagen.

TABLE 1

DSC Data for Irradiated Collagen.

| | | Weight of sample | Main peak melting temp. (° C.) | Onset temp. (° C.) | Delta H (J/g) | Program speed (° C./min) |
|---|---|---|---|---|---|---|
| Non-irradiated injectable collagen HUMALLAGEN ™ | Run 1 | 24.215 | 51.580 | 50.140 | 2.569 | 5.0 |
| | Run 2 | 24.902 | 51.450 | 50.040 | 2.660 | 5.0 |
| | Run 3 | 24.780 | 51.150 | 49.300 | 2.301 | 5.0 |
| | Run 4 | 25.356 | 51.310 | 49.460 | 2.348 | 5.0 |
| | Avg. | 24.813 | 51.373 | 49.735 | 2.470 | 5.0 |
| Injectable collagen HUMALLAGEN ™ was irradiated at 25 kGy in dry ice | Run 1 | 24.360 | 46.360 | 43.870 | 2.443 | 5.0 |
| | Run 2 | 25.005 | 46.700 | 44.300 | 2.599 | 5.0 |
| | Run 3 | 25.495 | 46.360 | 43.860 | 2.531 | 5.0 |
| | Avg. | 24.953 | 46.473 | 44.010 | 2.524 | 5.0 |

Table 1 shows that there is no peak below 36° C. for both non-irradiated and irradiated injectable collagen (HUMALLAGEN™) at 25 kGy in dry ice. This indicates that there is no denatured material present in the non-irradiated sample. Table I also demonstrates that there is no denatured material generated during the irradiation process. There was a slightly larger shoulder at 36° C.-40° C. for the irradiated injectable collagen (HUMALLAGEN™) when it was compared with non-irradiated injectable collagen (HUMALLAGEN™). This indicates that there is not a significant amount of degraded material generated during the irradiation. There was a slightly larger area at 40° C.-45° C. for the irradiated HUMALLAGEN™ when it was compared with non-irradiated injectable collagen (HUMALLAGEN™). This indicates that there is not a significant amount of Nonfibrillar collagen or thin fiber materials present in the irradiated injectable collagen. There is a difference between the main melting temperature of the non-irradiated injectable collagen (HUMALLAGEN™), 51.373° C., and the irradiated injectable collagen (HUMALLAGEN™), 46.473° C. This indicates that there is a collagen fiber class shifting. Although the impact of this shifting on the efficacy of the product is unknown, this shifting in melting temperatures demonstrates a significant alteration on the nature of the material after irradiation at 25 kGy dose in dry ice. This data demonstrates that irradiation at 25 kGy dose does not provide optimal injectable collagen product (HUMALLAGEN™).

Example 2

Injectable Collagen Product, HUMALLAGEN™, are Sterilized with Irradiation at 6 kGy and 12 kGy Materials and Methods Small batches of injectable collagen products with or without additional stabilizer were made, starting from a 3 mg/ml collagen solution, filtered through a 0.45 µm filter and reconstituted to injectable collagen material as in the first example. Products containing 1% sodium hyaluronate, 10 mM mannose or 10 mM sodium ascorbate as stabilizers were prepared separately. These materials were loaded into 1 cc glass syringes, and then irradiated at 6, 12, and 30 kGy in dry ice as in example 1. A parallel experiment was carried out in the absence of freezing for all same samples, in order to show the specific beneficial effect of freezing to protect the collagen molecules from irradiation damage. The same methods were used as described in example 1.

Results and Discussion

As in example 1, the color of the glass syringe turned to light brown at all doses of irradiation. The content of the syringe appeared homogeneous, without significant phase separation between a water phase and the collagen mass for all samples at all doses of irradiation. The content for all samples could be extruded through a fine gauge needle. The SDS-PAGE data revealed that the collagen molecules were protected significantly by the frozen condition during the gamma ray irradiation at 30 kGy. Only approximately 15% of the total of the collagen material was degraded. Optimal results were shown at 6 or 12 kGy doses. The degradation of samples at these doses was equivalent to the control sample without irradiation. The addition of stabilizer gives some additional protection but was not significant.

TABLE 2

DSC data for Irradiated Collagen with and without Stabilizers.

| | Weight of sample | Main peak temp. (° C.) | Onset temp. (° C.) | Delta H (J/g) | Program speed (° C./min) |
|---|---|---|---|---|---|
| Control, non-irradiated injectable collagen | 31.399 | 50.649 | 48.715 | 2.317 | 5.0 |
| Injectable collagen was irradiated at 6 kGy in dry ice | 23.586 | 50.932 | 46.443 | 2.014 | 5.0 |
| Injectable collagen with 1% Na Hyaluronate was irradiated at 6 kGy in dry ice | 19.828 | 49.999 | 47.212 | 2.028 | 5.0 |
| Injectable collagen with 10 mM sodium ascorbate was irradiated | 26.051 | 50.756 | 44.231 | 1.975 | 5.0 |

TABLE 2-continued

DSC data for Irradiated Collagen with and without Stabilizers.

| | Weight of sample | Main peak temp. (° C.) | Onset temp. (° C.) | Delta H (J/g) | Program speed (° C./min) |
|---|---|---|---|---|---|
| Injectable collagen with 10 mM mannose was irradiated at 6 kGy in dry ice | 17.865 | 46.322 | 41.000 | 1.988 | 5.0 |
| Injectable collagen was irradiated at 12 kGy in dry ice | 28.038 | 47.180 | 44.000 | 2.170 | 5.0 |

The DSC analysis of the collagen samples found that there is no peak below 36° C. for both control and treated samples. This indicates that there is no denatured material generated during the irradiation process. A slightly larger shoulder was observed at 36° C.-40° C. for the all treated samples when compared with control sample. This indicates that there is some degraded material generated during the irradiation at all doses. A slightly larger area at 40° C.-45° C. for the treated samples was observed when compared with the control sample. This indicates that there is some nonfibrillar collagen or thin fiber material present in the all irradiated samples. For treated groups: injectable collagen material irradiated at 6 kGy in dry ice, injectable collagen with 1% sodium hyaluronate irradiated at 6 kGy in dry ice, and injectable collagen with 10 mM sodium ascorbate irradiated at 6 kGy in dry ice, resulted in sterilized collagen material that retain all desirable attributes of the material. The main peak for these samples is the same as for the control sample at >50° C. This indicates that there is no significant collagen fiber class shifting in these samples. This data demonstrates that injectable collagen irradiated at 6 kGy in dry ice, injectable collagen with 1% sodium hyaluronate irradiated at 6 kGy in dry ice, and injectable collagen with 10 mM sodium ascorbate irradiated at 6 kGy in dry ice, are desirable conditions for sterilizing injectable collagen products such as HUMALLAGEN™. Injectable collagen irradiated at 12 kGy in dry ice has a main peak of melting temperature of 47.180° C.; it is 3.469° C. lower than the control sample's main peak of melting temperature at 50.649° C. and is on the end of the acceptable ranges for melting temperatures.

All samples irradiated at each of the three doses, without freezing, were significantly damaged. Two phases were distinctly separated within all the syringes. The collagen gel had shrunk and was surrounded by a fluid aqueous phase It was impossible to extrude the collagen gels from the syringes even with large needles. The SDS electrophoresis and DSC data demonstrate significant alteration of the collagen molecules.

Example 3

Injectable Collagen Product, HUMALLAGEN™, are Sterilized with Irradiation at 6 kGy and 8 kGy Injectable collagen product (HUMALLAGEN™) was irradiated in dry ice at 6 and 8 kGy. Non-frozen and non-irradiation samples were used as controls. The same methods were used as described in example 1.

As in examples 1 and 2, the color of the glass syringe turned to light brown following irradiation. The content of the syringe appeared homogeneous, without significant phase separation between a water phase and the collagen mass for all samples. The content could be extruded through a 30 g needle. The collagen molecules were protected significantly by the frozen condition during the gamma irradiation as determined by SDS-PAGE analysis. The data demonstrate that 6 to 8 kGy of irradiation do not result in degraded material in the collagen samples.

Table 3. DSC Data for Irradiated Samples.

TABLE 3

DSC Data for Irradiated Samples

| | Weight of sample | Main peak temp. (° C.) | Onset temp. (° C.) | Delta H (J/g) | Program speed (° C./min) |
|---|---|---|---|---|---|
| Control, non-irradiated Injectable collagen HUMALLAGEN™ | 25.059 | 50.462 | 49.002 | 2.267 | 5.0 |
| Injectable collagen HUMALLAGEN™ was irradiated at 6 kGy in dry ice | 24.211 | 49.307 | 47.157 | 2.423 | 5.0 |
| Injectable collagen HUMALLAGEN™ was irradiated at 8 kGy in dry ice | 24.448 | 48.780 | 46.754 | 2.351 | 5.0 |

The DSC data show that there is no peak below 36° C. for both control and treated samples. This indicates that no denatured materials were generated during the irradiation process. A slightly larger shoulder was observed at 36° C.-40° C. for the all treated samples when compared with control sample. This indicates that there is some degraded material generated during the irradiation. A slightly larger area was observed at 40° C.-45° C. for the treated samples when compared with control sample. This indicates that there is some Nonfibrillar collagen or thin fiber material present in all irradiated samples. The main peak for the sample irradiated with 6 kGy is 49.307° C. it is only 1.155° C. lower than the 50.462° C. for the control. This is not significant. The main peak for the Injectable collagen (HUMALLAGEN™) irradiated at 8 kGy in dry ice is 48.780° C.; it is only 1.682° C. lower than the 50.462° C. for the control. This is not significant. This data indicates that there is no significant collagen fiber class shifting in both irradiated samples. Therefore, irradiation at 6 kGy or 8 kGy in dry ice results in sterilization of injectable collagen products without adverse effects.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

We claim:

1. A method for sterilizing a collagen dermal filler consisting of:
   a) freezing the collagen dermal filler and
   b) irradiating the frozen collagen dermal filler with an effective amount of gamma or e-beam radiation of between 6 kGy and 8 kGy to sterilize the dermal filler.

2. The method of claim 1 wherein the collagen is selected from the group consisting of recombinant human collagen, tissue engineered human-based collagen, porcine collagen, human placental collagen, bovine collagen, autologous collagen, collagen fibers, and human tissue collagen matrix.

3. The method of claim 2 wherein the collagen is selected from the group consisting of recombinant human collagen type I, II, or III, isolated human-based collagen type I preparations, isolated human-based collagen type III, porcine collagen type I, porcine collagen type III, human type I, II, III or IV placental collagen, solubilized elastin peptides with bovine collagen, bovine dermal collagen cross-linked by glutaraldehyde, collagen fibers, human tissue collagen matrix derived from cadaveric dermis, acellular human cadaveric dermis that has been freeze-dried and micronized, globin (the protein portion of hemoglobin) and cultured autologous fibroblasts.

4. The method of claim 1 wherein the dermal filler further comprises a stabilizer selected from the group consisting of mannitol, mannose, ascorbic acid, hyaluronic acid, saccharides, polysaccharides, sodium hyaluronate, and sodium ascorbate.

5. The method of claim 1 wherein the radiation is e-beam irradiation.

6. The method of claim 1 wherein the radiation is gamma irradiation.

7. The method of claim 1 wherein the freezing temperature is −80° C.

8. The method of claim 1 wherein biological contaminants or pathogens are removed from the collagen prior to freezing.

9. The method of claim 1 wherein the dermal filler achieves a sterility assurance level (SAL) of $10^{-6}$ SAL following irradiation.

10. A sterilized and injectable collagen dermal filler which is selected from collagen pastes, gels, solutions, and suspensions and prepared by the method consisting of:
    a) freezing the collagen dermal filler and
    b) irradiating the frozen collagen dermal filler with an effective amount of gamma or e-beam radiation of between 6 kGy and 8 kGy to sterilize the dermal filler.

11. The filler of claim 10 comprising collagen selected from the group consisting of recombinant human collagen, tissue engineered human-based collagen, porcine collagen, human placental collagen, bovine collagen, autologous collagen, collagen fibers, and human tissue collagen matrix.

12. The filler of claim 11 wherein the collagen is selected from the group consisting of recombinant human collagen type I, II, or III, isolated human-base collagen type I preparations, isolated human-based collagen type III, porcine collagen type I, porcine collagen type III, human type I, II, III or IV placental collagen, solubilized elastin peptides with bovine collagen, bovine dermal collagen cross-linked by glutaraldehyde, collagen fibers, human tissue collagen matrix derived from cadaveric dermis.

13. The filler of claim 10 further comprising a stabilizer selected from the group consisting of mannitol, mannose, ascorbic acid, hyaluronic acid, saccharides, polysaccharides, sodium hyaluronate, and sodium ascorbate.

14. The filler of claim 10 wherein the dermal filler achieves a sterility assurance level (SAL) of $10^{-6}$ SAL following irradiation.

* * * * *